United States Patent
Loeb

(10) Patent No.: US 6,432,413 B1
(45) Date of Patent: Aug. 13, 2002

(54) FUNCTIONAL IMPROVEMENTS IN FAHR DISEASE

(75) Inventor: Jeffrey A. Loeb, Beverly Hills, MI (US)

(73) Assignee: Wayne State University, Detroit, MI (US)

(*) Notice: Subject to any disclaimer, the term of this patent is extended or adjusted under 35 U.S.C. 154(b) by 0 days.

(21) Appl. No.: 09/260,376

(22) Filed: Mar. 1, 1999

Related U.S. Application Data

(60) Provisional application No. 60/076,287, filed on Feb. 27, 1998.

(51) Int. Cl.[7] .......................... A61K 9/00; A61F 13/00; A01N 33/18
(52) U.S. Cl. ....................... 424/400; 424/435; 514/742
(58) Field of Search ............................... 424/400, 435; 514/742

(56) References Cited

U.S. PATENT DOCUMENTS

| | | | |
|---|---|---|---|
| 3,553,314 A | 1/1971 | Francis | 424/49 |
| 3,553,315 A | 1/1971 | Francis | 424/49 |
| 3,584,124 A | 6/1971 | Francis | 424/204 |
| 3,584,125 A | 6/1971 | Francis | 424/204 |
| 3,641,246 A | 2/1972 | Francis | 424/204 |
| 3,662,066 A | 5/1972 | Francis | 424/204 |
| 3,678,164 A | 7/1972 | Francis | 424/204 |
| 3,683,080 A | 8/1972 | Francis | 424/204 |
| 3,962,433 A | 6/1976 | Worms et al. | 424/212 |
| 4,216,211 A * | 8/1980 | Francis | 424/204 |
| 5,854,071 A * | 12/1998 | Oppermann et al. | 435/353 |
| 5,898,038 A * | 4/1999 | Yallampalli et al. | 514/742 |

OTHER PUBLICATIONS

Berger et al., "Reversible Parkinson Syndrome Complicating Postoperative Hypoparathyroidism," Neurology 31:881–882 (1981).
Boller et al., "Familial Idiopathic Cerebral Calcifications," J. Neurol. Neurosurg. and Psychiatry 40:280–285 (1977).
Fleisch, "Bisphosphonates: A New Class of Drugs in Diseases of Bone and Calcium Metabolism," Recent Results in Cancer Res. 116:1–28 (1989).
Frame, "Parkinsonism in Postoperative Hypoarathyroidism," Arch. Intern. Med. 116:424–427 (1965).
Lowenthal et al., "Striopallidodentate Calcification," Handbook of Clin. Neurol. 6:712–716 (1968).
Lowenthal, "Striopallidodentate Calcifications," Handbook of Clin. Neurol. 5:417–436 (1986).
Moskowitz et al., "Familial Calcification of the Basal Ganglions: A Metabolic and Genetic Study," New. Engl. J. Med. 285:72–77 (1971).
Smeyers–Verbeke et al., "The Chemical Composition of Idiopathic Nonarteriosclerotic Cerebral Calcifications," Neurology 25:48–57 (1975).

* cited by examiner

Primary Examiner—Thurman K. Page
Assistant Examiner—S. Tran
(74) Attorney, Agent, or Firm—Clark & Elbing LLP

(57) ABSTRACT

The invention provides methods of treating diseases of the central and peripheral nervous systems that are associated with abnormal calcifications within the nervous system, such as Fahr disease. These methods involve administration of bisphosphonates, such as disodium etidronate, to patients.

4 Claims, 3 Drawing Sheets

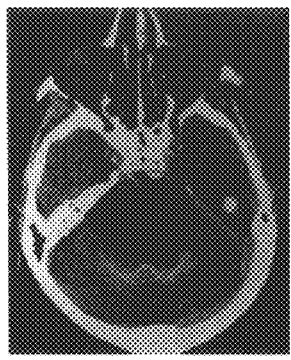 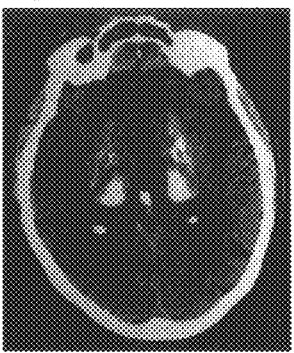  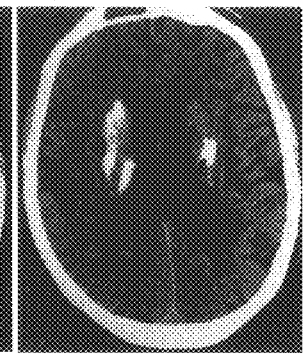
FIG. 1A  FIG. 1B  FIG. 1C  FIG. 1D
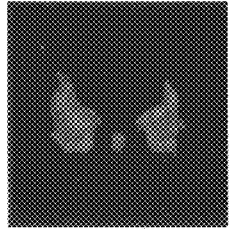 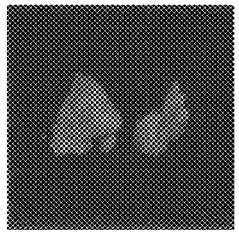 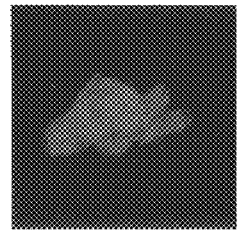 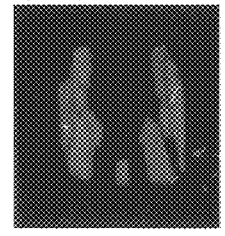
FIG. 1E  FIG. 1F  FIG. 1G  FIG. 1H

FUNCTIONAL IMPROVEMENTS IN FAHR DISEASE

This application claims priority from U.S. Ser. No. 60/076,287, which was filed on Feb. 27, 1998.

BACKGROUND OF THE INVENTION

This invention relates to methods for treating diseases of the central and peripheral nervous systems.

There is a remarkable propensity for accumulation of calcium and other multivalent cations in the basal ganglia and dentate nucleus of man. In a majority of cases, calcium deposits are asymptomatic, but there are still many cases in which a devastating, slowly progressive Parkinson-like disorder is associated with dense coalescence of calcium deposits into "brain stones" (1). Pathologically, brain stones are found mostly in the grey matter of the basal ganglia, and chemical analysis reveals that they are composed mostly of hydroxyapatite, which is the same calcium-phosphate structure of normal bone (1, 2).

Such cerebral calcifications have been associated with hypoparathyroidism, mitochondrial myopathies, and an idiopathic, familial form of basal ganglia calcification that often carries the eponym of Fahr Disease (1–4). In Fahr disease, cerebral calcification is observed in teenage children, however, patients do not begin developing progressive parkinsonian and psychiatric symptoms until reaching their 30's and 40's. No clear underlying defect in calcium or phosphate metabolism has been established for these patients, and there is, as yet, no treatment for the progressive neurologic deterioration of this disease.

Bisphosphonates are a class of drugs that resemble pyrophosphoric acid and are used for treatment of diseases of bone and calcium metabolism (5). They have been used with variable success for ectopic, subcutaneous calcification, and are generally considered to be safe, with few side effects. In vitro, bisphosphonates have been shown to have a high affinity for solid-phase calcium phosphate, and thereby inhibit both the formation and dissolution of hydroxyapatite.

SUMMARY OF THE INVENTION

I have found that a class of drugs, called bisphosphonates, and the specific drug, disodium etidronate, are useful therapeutic agents for diseases of the human central and peripheral nervous systems that are associated with abnormal calcifications within the nervous system.

Accordingly, the invention provides methods of treating a patient having a disease of the nervous system characterized by abnormal calcification, by administering a bisphosphonate the patient. Treatment according to the methods of the invention results in improvement of a symptom(s) of a treated patient.

Patients that can be treated using the methods of the invention include those at all stages of development of a disease of the nervous system characterized by calcification within the nervous system. For example, treatment of an older patient with Fahr disease is described in detail below. Treatment of younger, less disabled patients with this disorder offers an alternative, more favorable course to an otherwise devastating neurologic disease.

An example of a bisphosphonate that can be used in the methods of the invention is disodium etidronate, which can be administered, for example, orally in an amount between 5–20 mg/kg/day (e.g., 10–15 mg/kg/day). Other bisphosphonates are known in the art, and can be used in the methods of the invention. For example, pamidronate, risedronate, ibandronate, olpadronate, incadronate, neridronate, tiludronate, can be used, and proper modes of administration (e.g., oral or intravenous infusion) and dosages of these drugs are known to those of skill in the art. Administration of combinations of these drugs can also be carried out.

In the methods of the invention, bisphosphonates are used to treat diseases of the nervous system in which calcifications occur within the nervous system. The mechanism of action of these agents in treating these diseases is to prevent the further growth of calcifications, and to reduce neurological symptoms related to the calcifications. Used in this fashion, bisphosphonates improve neurological function, reduce seizures, and improve abnormal behaviors.

An example of a particular disease that can be treated by the methods of the invention is Fahr disease, which is characterized by idiopathic cerebral calcification of the basal ganglia. Other examples of diseases of the nervous system that can be treated with bisphosphonates according to the invention are as follows: post-radiation-induced calcifications of the brain; post-stroke/hypoxemic calcifications; calcified brain tumors, primary and metastatic; neurocysticercosis; human immunodeficiency virus (HIV)-induced calcifications of the brain; cytomegalovirus infection; cryptococcosis of the central nervous system; other post-infectious calcifications of the brain (e.g., as is found in tuberculosis and toxoplasmosis); metabolic disease-induced cerebral calcification; endocrine disease-induced cerebral calcification (hypoparathyroidism, etc.); celiac disease; mitochondrial encephalomyopathies; subdural hematoma with calcifications; other seizure disorders associated with cerebral calcifications; arteriovenous malformations of the brain; cerebral lupus and other forms of vasculitis associated with cerebral calcifications; and presenile dementia with associated cerebral calcifications.

Other features and advantages of the invention will be apparent from the following detailed description, the drawings, and the claims.

BRIEF DESCRIPTION OF THE DRAWINGS

FIG. 1 is a series of axial CAT scans and 3-dimensional reconstructions of basal ganglia calcification. Panels A–D show the extent of cerebral calcification on axial CAT scan images showing involvement of the basal ganglia, thalamus, and cerebellum. Panels E–H are 3-dimensional reconstructions of the basal ganglia, thalami, and pineal gland in different projections. The patient is directly facing the viewer in Panel E, turning to the left by 30 degrees in Panel F, and by 60 degrees in Panel G. Panel H is a projection looking from above and behind the patient, in the same orientation as the CAT scans described above. Three-dimensional reconstructions were produced by combining consecutive, 3 mm coronal images with pixels of 50 Hounsfield units or more using General Electric Advantage software.

Figure 2:
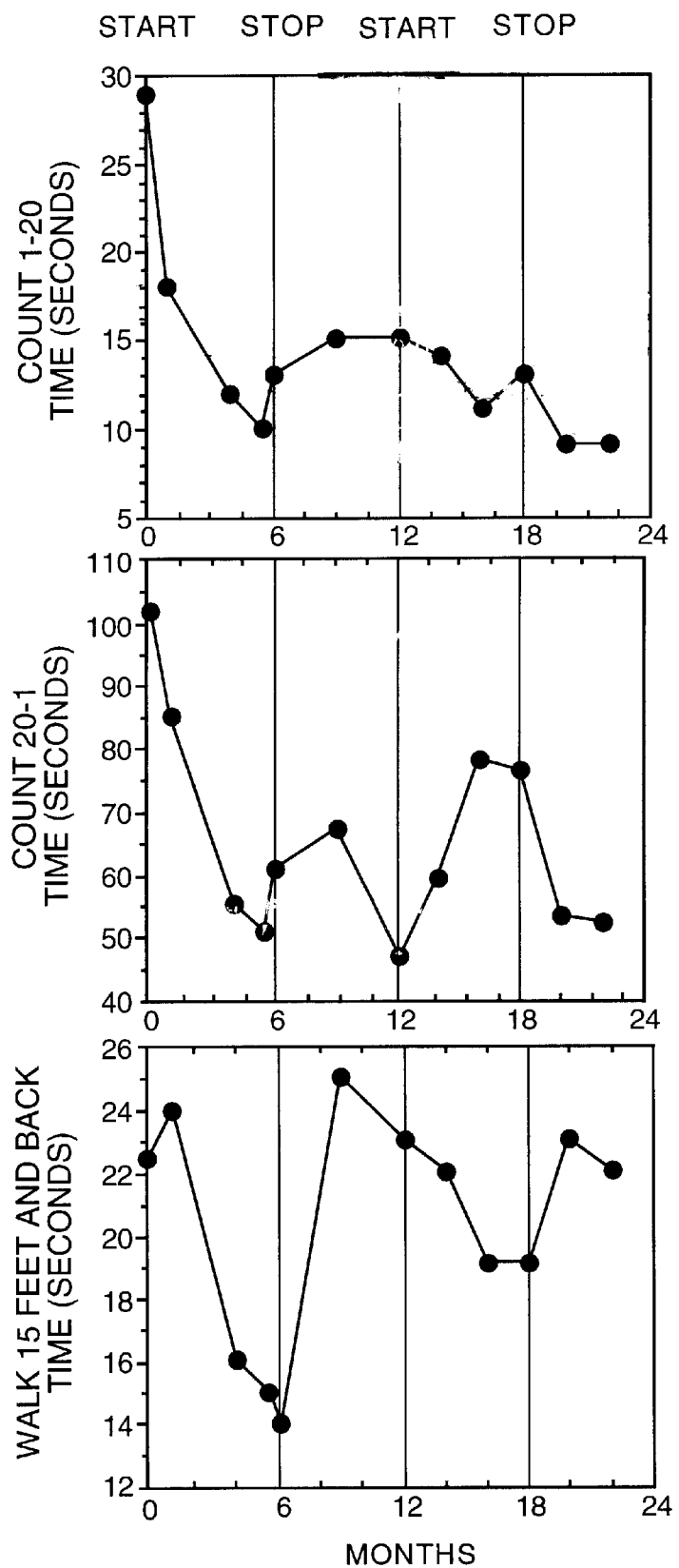
FIG. 2 is a series of graphs showing the effect of treatment on speech and gait. Timed measurements of speech (counting from 1–20 or 20–1) and gait (walking 15 feet and back) were made during two treatment cycles with disodium etidronate. The start and stop times indicate the times at which the medication was begun and discontinued, respectively. Each zero time point for counting 1–20 and walking 15 feet and back represents an average of 2 separate measurements, taken 2 weeks apart.

Quantitative measurements of cerebral calcification were obtained using contiguous regions of calcification, defined as those containing pixels greater than 50 Hounsfield units, on each 3 mm coronal image. An increase in Hounsfield units corresponds to an increase in calcific density. The average density (expressed in Hounsfield units) for each of these regions was multiplied by the area (in pixels) to give an estimate of both the density and extent of the calcification. Each of these (density x area) measurements were summated for the right basal ganglia and thalamus, left basal ganglia and thalamus, and cerebellum, as is indicated by different shadings.

DETAILED DESCRIPTION

The invention provides methods for treating diseases of the human central and peripheral nervous systems that are associated with abnormal calcifications within the nervous system. These methods involve administration of a bisphosphonate, such as disodium etidronate, to a patient. For example, disodium etidronate can be administered to a patient one time per day, orally, in amounts ranging from 5–20 mg/kg/day (e.g., 10–15 mg/kg/day), given for up to a maximum of 6 months. Retreatment after a 90 day minimum period off of the medication can be carried out, to maintain improved function and prevent growth of calcifications.

The invention is exemplified, as follows, with a description of the treatment of a patient with Fahr disease with the bisphosphonate disodium etidronate. Because of the structural similarity of brain stones, which are characteristic of Fahr disease, to bone, disodium etidronate was given to a patient with familial, idiopathic cerebral calcinosis of the basal ganglia, in the hope that it would bind to the cerebral calcification and prevent further neurologic deterioration.

The patient is a 59 year old man with hypertension and osteoarthritis who presented at age 50 with transient right hemiparesis and dysarthria. He recovered, but one year later had a similar episode without full recovery. Since then, he has had a gradual decline in motor function. His major neurologic disabilities prior to treatment were slowness of gait and speech, rigidity, spasticity, cerebellar ataxia, dystonia, and dysphagia. He scored 6 points out of a possible 37 points on the right side of the Blessed Dementia Scale, which measures memory and concentration (6). A score of 0 points is without error. He had been having frequent emotional outbursts and inappropriate hypersexuality.

His father died of a cerebral hemorrhage and his mother died of a stroke. He has 7 brothers and 2 sisters, of which only one of his brothers was imaged documenting cerebral calcification associated with dysarthria and bradykinesia.

His baseline work-up included CAT scans of the brain, which demonstrated dense bilateral calcification involving basal ganglia (caudate, putamen, and globus pallidus), thalamus, dentate nuclei of the cerebellum, and, to a lesser extent, internal capsule (FIG. 1). He had normal serum levels of calcium, phosphate, and parathyroid hormone. A bone scan of the head using a technetium-labeled bisphosphonate did not reveal uptake into his cerebral calcification, possibly because of high signal in the surrounding bone. He had previously been treated with many drugs, with minimal improvement, including carbidopa-levodopa, baclofen, pergolide, lorazepam, dantrolene, and bromocriptine. Prior to initiating and throughout the study, he was maintained on the same doses of baclofen, pergolide, lorazepam, naproxen, diltiazem, probanthiline bromide, and hyoscyamine sulfate. He was placed on isosorbide dinitrate 2 months into the study for ischemic heart disease.

After obtaining baseline measurements and informed consent, the patient was begun on 15 mg/kg of disodium etidronate given once daily for two 6 month periods, separated by a 6 month period off of the drug, which was carried out as an internal control and to allow for normal bone mineralization. Serial neurologic examinations were performed by the same physician, and included three quantitative measurements: counting from 1–20, counting from 20–1, and walking 15 feet and back. Instructions were given with the same amount of encouragement for each of the serial measurements. Duplicate measures of counting 1–20 and walking taken two weeks apart were averaged to produce baseline values. There was little variation between the duplicate measures. Baseline and follow-up videotapes of the neurologic exam and CAT scans, to quantify the amount of cerebral calcification, were obtained in a uniform manner.

After the patient had been taking disodium etidronate for one month, the patient's family felt that his speech had become clearer, his attention span improved, and his emotional outbursts and inappropriate sexual behavior ceased. He experienced no side effects from the medication, except for transient elevations in serum phosphate. Prior to treatment with disodium etidronate, he had a severe, mixed dysarthria with components of spasticity, hypokinesia, dyskinesia, and ataxia. Within four months, his speech became more rapid and clear, so that others could now understand what he was saying. His gait also improved, together with fine motor skills. For example, he could button his shirts, which he could not do previously.

FIG. 2 shows the results of an analysis of three quantitative parameters used to assess his rate of speech and ambulation. Over the first six months of treatment, he showed a two-fold increase in the speed of his speech and gait.

Improvements in his rate of speech and movement were confirmed by videotape analysis before and after treatment. After stopping the medication, he had a significant deterioration in his gait, but little loss in the gains made with his speech. A second six month course of treatment was then initiated, with less dramatic effects. While his gait again improved, his speech, which did not worsen significantly when he was off of the medication, did not change appreciably. There was improvement in counting from 1–20, but some deterioration in counting from 20–1.

Other measurements of the speed of motor movement also improved considerably, as is shown in videotape recorded before starting medication and at the end of the first six month treatment. They included rapid finger tapping and knee patting. These were not made serially and hence not practiced. Eighteen months after beginning treatment, he scored 2 on the Blessed Dementia Scale, up from his previous score of 6. While his bradykinesia and emotional lability clearly improved, his spasticity, cerebellar ataxia, and dystonia were unchanged.

Figure 3:
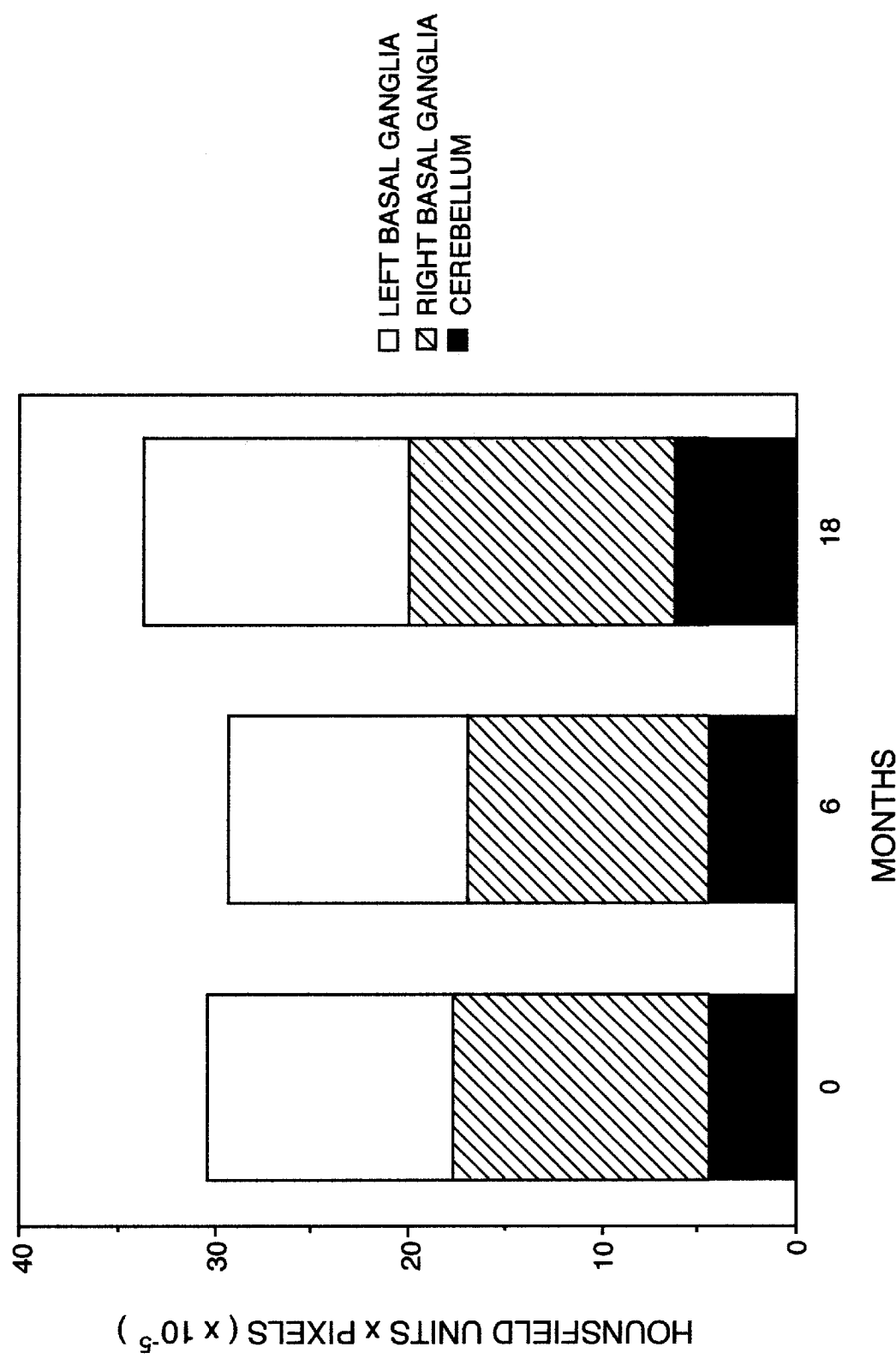
FIG. 3 is a graph showing quantitation of cerebral calcification. Serial CAT scans were obtained prior to treatment (0 months) and after the first (6 months) and second (18 months) treatment cycles with sodium etidronate.

Quantitative measurements from serial CAT scans of the brain before treatment and after the first and second treatment periods did not show any reduction in brain calcium content, but perhaps a small increase (FIG. 3). Similarly, a qualitative comparison of the CAT scans and 3-dimensional reconstructions of the basal ganglia calcification, as is shown in FIG. 1, did not demonstrate any change in the shape and size of the cerebral calcification after treatment. Thus, his functional improvements could not be attributed to a reduction in the extent or density of cerebral calcification.

Thus, I have described the first case of sustained, symptomatic improvement in a patient with familial, idiopathic cerebral calcification using a bisphosphonate. Previous efforts using calcium chelators in Fahr Disease have been unsuccessful (4). Following treatment, the patient improved significantly in his bradykinesia, dysarthria, and emotional lability, while his spasticity, ataxia, and dystonia were unchanged. Despite clinical improvement, quantitative CAT scan data did not show any reduction in the amount of cerebral calcification.

To reduce the possibility of a placebo effect, two trials of disodium etidronate were given followed by equal periods off of this medication. The most dramatic effects occurred within the first six month treatment period. While the speed of the patient's speech remained improved when he was off of medication, the speed of his gait deteriorated significantly, and improved again after the second 6 month trial. The improvements noted in the velocity of movements occurred with these three serially measured parameters, but also with several parameters such as finger tapping and knee patting, not followed serially. These results show that the patient's improvements were not due to placebo or practice effects.

Patients with long-standing hypoparathyroidism can develop a very similar syndrome of parkinsonism associated with dense basal ganglia calcification (7, 8). Some of these patients have improved dramatically after treatment of the hypoparathyroidism with calcium and vitamin D. Similar to the patient described here, the extrapyramidal symptoms appear to be most easily reversed.

Since there was no reduction in the extent of cerebral calcification, an alternative explanation is needed to account for the clinical improvement. Pathological studies on patients with Fahr Disease reveal normal appearing neurons directly adjacent to brain stones in the basal ganglia (9). These neurons may be reversibly damaged by high local calcium concentrations, perhaps via a glutamate receptor-mediated neurotoxicity. By virtue of its tight association with hydroxyapatite surfaces, the bisphosphonate may effectively reduce the calcium concentration adjacent to these neurons, thereby improving neuronal function. An alternative explanation is that the patient's improvement stems from altering calcium and phosphate homeostasis peripherally.

REFERENCES

1. Lowenthal A., "Striopallidodentate calcification," *Handbook of Clin. Neurol.* 1986; 5:417–436.
2. Smeyers-Verbeke J., Michotte Y., Pelsmaeckers J., Lowenthal A., Massart D. L., Dekegel D., and Karcher D., "The chemical composition of idiopathic nonarteriosclerotic cerebral calcification," *Neurology* 1975; 25:48–57.
3. Moskowitz M. A., Winickoff R. N., and Heinz E. R., "Familial calcification of the basal ganglions a metabolic and genetic study," *New Engl. J. Med.* 1971; 285:72–77.
4. Boller F., Boller M., and Gilbert J., "Familial idiopathic cerebral calcification," *J Neurol. Neurosurg. and Psychiatry* 1977; 40:280–285.
5. Fleisch H., "Bisphosphonates: a new class of drugs in diseases of bone and calcium metabolism," *Recent Results in Cancer Res.* 1989; 116:1–28.
6. Roth M., Tomlinson B. E., and Blessed G., "The relationship between quantitative measures of dementia and of degenerative changes in the cerebral grey matter of elderly subjects," *Proc. R. Soc. Med.* 1967; 60:254–260.
7. Frame B., "Parkinsonism in postoperative hypoparathyroidism," *Arch. Intern. Med.* 1965; 116:424–427.
8. Ross D. B. and Berger J. R., "Reversible parkinson syndrome complicating postoperative hypoparathyroidism," *Neurology* 1981; 31:881–882.
9. Lowenthal A. and Bruyn G. W., "Striopallidodentate calcification," *Handbook of Clin. Neurol.* 1968; 6:712–716.

What is claimed is:

1. A method of treating a patient having a disease of the central nervous system that is characterized by the existence of abnormal calcification in the nervous system, wherein said disease is Fahr disease, said method comprising administering a bisphosphonate to said patient.

2. The method of claim 1, wherein said bisphosphonate is disodium etidronate.

3. The method of claim 1, wherein said bisphosphonate is orally administered to said patient.

4. The method of claim 1, wherein said bisphosphonate is administered to said patient in a daily dose of 5–20 mg/kg.

* * * * *